United States Patent

Tsukada et al.

Patent Number: 5,481,048
Date of Patent: Jan. 2, 1996

[54] METHOD FOR PREPARING COPPER-CONTAINING HYDROGENATION REACTION CATALYST AND METHOD FOR PRODUCING ALCOHOL

[75] Inventors: Kiyoshi Tsukada; Yasuyuki Hattori; Taku Mimura, all of Wakayama, Japan

[73] Assignee: Kao Corporation, Tokyo, Japan

[21] Appl. No.: 357,173

[22] Filed: Dec. 13, 1994

[30] Foreign Application Priority Data

Dec. 13, 1993 [JP] Japan ................................. 5-342536

[51] Int. Cl.⁶ ..................... C07C 29/36; C07C 31/125
[52] U.S. Cl. ..................... 568/885; 568/814; 568/864; 568/865; 568/884
[58] Field of Search ............................. 568/864, 814, 568/830, 861, 862, 885, 884, 811, 831; 502/345

[56] References Cited

U.S. PATENT DOCUMENTS

| | | | |
|---|---|---|---|
| 4,278,567 | 7/1981 | Miya | 252/466 |
| 4,780,448 | 10/1988 | Broecker et al. | 502/244 |
| 4,794,098 | 12/1988 | Pohl et al. | 502/172 |
| 4,829,039 | 5/1989 | White et al. | 502/152 |
| 4,918,248 | 4/1990 | Hattori et al. | 568/885 |
| 4,954,146 | 9/1990 | Garrett et al. | 55/25 |
| 5,030,609 | 7/1991 | Turner et al. | 502/318 |
| 5,229,346 | 7/1993 | Mori et al. | 502/302 |
| 5,233,099 | 8/1993 | Tabata et al. | 568/885 |
| 5,233,100 | 8/1993 | Tabata et al. | 568/885 |
| 5,345,005 | 9/1994 | Thakur et al. | 568/885 |
| 5,395,990 | 3/1995 | Scarlett | 568/864 |
| 5,406,004 | 4/1995 | Eastland et al. | 568/864 |

FOREIGN PATENT DOCUMENTS

| | | |
|---|---|---|
| 0507658 | 10/1992 | European Pat. Off. . |
| 2161699 | 7/1973 | France . |
| 2172303 | 9/1973 | France . |
| 1768313 | 5/1977 | Germany . |
| 3443277 | 6/1985 | Germany . |
| 47014113 | 1/1974 | Japan . |
| 83050775 | 11/1983 | Japan . |
| 61-161146 | 7/1986 | Japan . |
| 61-178037 | 8/1986 | Japan . |
| 62-298457 | 12/1987 | Japan . |
| 1127042 | 5/1989 | Japan . |
| 1305042 | 12/1989 | Japan . |
| 2026611 | 1/1990 | Japan . |
| 5117185 | 5/1993 | Japan . |
| 5177140 | 7/1993 | Japan . |
| 385625 | 4/1930 | United Kingdom . |

Primary Examiner—Werren B. Lone
Attorney, Agent, or Firm—Birch, Stewart, Kolasch & Birch

[57] ABSTRACT

A copper-containing hydrogenation reaction catalyst is prepared by reducing a precursor of a copper-containing catalyst usable in hydrogenation reaction with hydrogen gas or a mixture of hydrogen and an inert gas by liquid phase reduction in a stream of a solvent in the temperature range of from 50° to 140° C. An alcohol is produced using the catalyst thus obtained in a fixed bed continuous reaction system.

16 Claims, No Drawings

METHOD FOR PREPARING COPPER-CONTAINING HYDROGENATION REACTION CATALYST AND METHOD FOR PRODUCING ALCOHOL

BACKGROUND OF THE INVENTION

1. Field of the Invention

The present invention relates to a method for preparing a copper-containing catalyst usable in hydrogenation reaction, and to a method for producing an alcohol. More specifically, it relates to a method for preparing a copper-containing catalyst usable in a hydrogenation reaction (hereinafter referred to as a copper-containing hydrogenation reaction catalyst) by a liquid phase reduction under specified temperature conditions, and to a method for producing an alcohol of high quality at a high productivity using the copper-containing hydrogenation reaction catalyst which is prepared by the above method and which has markedly improved catalytic activity and selectivity.

2. Discussion of the Related Art

Since the 1930s a number of methods have been disclosed for producing aliphatic alcohols, alicyclic alcohols or aromatic alcohols by hydrogenating carboxylic acids or esters of carboxylic acids. In those methods, copper catalysts are mainly proposed for use in hydrogenation of esters of carboxylic acids, particularly fatty acid esters and copper-chromium catalysts are commonly used for industrial purposes.

Determination of the conditions employed to activate the precursors of these catalysts by reduction depends on the form and reduction method of the precursors, usage of the obtained catalysts, and other factors. For example, when the fluidized bed reaction system is used, a powder form is employed. In Japanese Patent Laid-Open Nos. 1-305042, 5-177140 and 5-117185, it is stated that a catalyst precursor may be activated by gas phase reduction or by liquid phase reduction in a solvent exemplified by hydrocarbons such as paraffin, ethers such as dioxane, alcohols, and esters. Gas phase reduction, however, requires an additional apparatus other than the reactor for reductive activation of a powdery catalyst precursor and further needs a surface stabilizing treatment for preventing the resulting copper from being oxidized by air. Because of these drawbacks of gas phase reduction, liquid phase reduction is generally employed in the fluidized bed reaction system. In this case, it is generally agreed that reduction is carried out preferably at a temperature of from 150° to 350° C. until hydrogen absorption has stopped. Since heat removal is easy in the case of a powdery form, local overheating can easily be prevented.

On the other hand, when a fixed bed reaction system is used, gas phase reduction is exclusively used for the reductive activation of a formed catalyst precursor, and, for industrial purposes, it is common practice to carefully reduce a catalyst precursor at a given temperature while supplying an inert gas containing several to several dozens percents of hydrogen, to prevent local overheating due to rapid reduction.

Reduction of copper oxide with hydrogen is generally known to generate a heat of reduction of 20 Kcal per mole of copper oxide and the reduced copper thus obtained has a very low thermal stability. For this reason, it is important to gradually reduce the copper oxide while controlling heat generation to prevent the deterioration of catalyst performance. When using a formed catalyst precursor, in particular, this is critical because heat removal is difficult.

It is, therefore, very liable that when a catalyst precursor is activated by gas phase reduction with a high concentration of hydrogen in a short time, a rapid heat generation considerably degrades catalyst performance, and that when a large amount of catalyst precursor is activated by reduction in a short time on an industrial scale, a rapid rise in temperature causes a very dangerous situation. For this reason, it is common practice to use a low concentration of hydrogen over a long period of time for activation of catalyst precursors containing copper oxide by gas phase reduction. For example, Japanese Patent Laid-Open No. 61-161146 states that it takes as long as 4 to 14 days for catalytic activation by such reduction, indicating a disadvantage of gas phase reduction in view of alcohol productivity.

Also, DT 1768313 discloses a method for reductive activation of a copper-zinc oxide catalyst precursor, in which the catalyst precursor is gradually reduced at a temperature of between 120° and 240° C. in a hydrogen-containing nitrogen gas stream and finally treated with high-pressure hydrogen at a temperature of from 250° to 300° C. for 1 to 2 hours. Japanese Patent Laid-Open No. 62-298457 states that a copper-chromium oxide catalyst precursor can be activated by raising a temperature from 130° C. to 200° C. at a rate of 10° C./hr and keeping it at 200° C. for 12 hours in a nitrogen gas stream containing 1% by volume hydrogen. Also, DE 3443277A1 discloses a method for reductive activation of a copper-zinc oxide catalyst precursor, in which the catalyst precursor is reduced at 200° C. in a nitrogen gas stream containing 5% by volume hydrogen for 16 hours and then further reduced with pure hydrogen at 200° C. for 16 hours. Japanese Patent Laid-Open No. 61-178037 states that a copper oxide-magnesium silicate catalyst precursor can be activated by reducing at 200° C. in a nitrogen gas stream containing 1 to 2% by volume hydrogen for 60 hours. In addition, Japanese Patent Laid-Open No. 1-127042, which discloses a method for reductive activation of copper-chromium oxide and reviews the prior arts, indicates that all methods require reduction temperatures of not lower than 150° C. for catalyst precursor activation.

Although gas phase reduction is commonly used in the fixed bed reaction system, several methods of liquid phase reduction are also known to activate a catalyst precursor containing copper oxide. For example, Japanese Patent Laid-Open Nos. 5-177140 and 5-117185 propose to activate a copper-zinc oxide catalyst precursor at 200° C. in an autoclave by a batch reaction method in liquid phase. Also, British Patent Publication No. 385625 describes a method of liquid phase reduction of a copper-chromium catalyst precursor at 325° C. in an ester flow of a liquid hourly space velocity of 8.0 in the fixed bed reaction system, followed by hydrogenation of the ester. Also, Japanese Patent Laid-Open No. 47-14113 discloses a method of liquid phase reduction of a precursor of copper-chromium catalyst at 200° C. in a lactone flow of a liquid hourly space velocity of 0.67 in the fixed bed reaction system, followed by hydrogenation of the lactone. According to Japanese Patent Laid-Open No. 2-26611, the reduction of a catalyst precursor containing copper oxide can be carried out after an ester, the starting material, has been supplied.

However, all these activation methods by liquid phase reduction have practically no advantages over those by gas phase reduction, as Japanese Patent Laid-Open No. 2-26611 states that "reduction of the catalyst's copper component by these methods is not complete and somewhat difficult to control."

According to the findings of the inventors, reductive activation with hydrogen at a temperature of 150° C. or higher under the stream of an ester or an alcohol has drawbacks as mentioned below.

When an ester is used as the solvent, hydrolysis of ester with water produced upon catalyst reduction occurs to produce fatty acids, catalyst poisons to copper-containing catalysts. Therefore, such esters cannot directly be used as a starting material for alcohol production. Also, fatty acids formed during the reductive activation of a catalyst precursor cause dissolution of copper and other problems leading to deterioration of the catalyst. When an alcohol is used as a solvent, as the reductive activation of a catalyst proceeds, an ester wax is formed from two alcohol molecules and causes a significant decrease in the purity of alcohol. In addition, the higher the temperature for activation is, the more hydrocarbons due to alcohol decomposition are formed, which also significantly decrease the purity of alcohol.

SUMMARY OF THE INVENTION

It is an object of the present invention to provide a method for preparing a copper-containing hydrogenation reaction catalyst with markedly improved catalytic activity and selectivity by liquid phase reduction.

It is another object of the present invention to provide a method for producing an alcohol of high quality at a high productivity using the copper-containing hydrogenation reaction catalyst prepared by the above method.

In an effort to achieve the above object, the present inventors have found that a copper-containing catalyst with higher activity can be obtained by liquid phase reduction without impairing catalytic activity in a shorter activation time than those by gas phase reduction methods which are widely used for industrial purpose. This can be achieved by contacting the precursor with hydrogen gas, or a mixture of hydrogen and an inert gas, in a solvent inert to copper oxide or metallic copper at a temperature of from 50° to 140° C., then, when organic carboxylic acid or esters thereof, preferably fats and oils or fatty acid esters, are hydrogenated in a fixed bed continuous reaction system to produce a corresponding alcohol. Based on this finding, the inventors have completed the present invention.

Specifically, the present invention relates to:

(1) a method for preparing a copper-containing hydrogenation reaction catalyst, comprising reducing a precursor of a copper-containing hydrogenation reaction catalyst with hydrogen gas, or a mixture of hydrogen and an inert gas, by liquid phase reduction in a stream of a solvent which does not react with copper oxide or metallic copper, wherein the liquid phase reduction is carried out in the temperature range of from 50° to 140° C.; and (2) a method for producing an alcohol, comprising reducing an organic carboxylic acid or an ester thereof by catalytic reduction with hydrogen in a fixed bed continuous reaction system comprising the copper-containing hydrogenation reaction catalyst prepared by the method of (1) above.

According to the method for preparing a copper-containing hydrogenation reaction catalyst of the present invention, a formed catalyst precursor containing copper oxide is activated by liquid phase reduction under specified conditions. By the present method, a catalyst with an improved catalytic activity can be prepared in a significantly shortened activation time without impairing the quality of solvent and catalytic performance. Therefore, the method for producing an alcohol of the present invention, using the above catalyst, makes it possible to produce an alcohol of high quality at a very high efficiency on an industrial scale.

DETAILED DESCRIPTION OF THE INVENTION

The present invention is described in detail below.

According to the method of the present invention, a copper-containing hydrogenation reaction catalyst is prepared by reducing a formed precursor of the copper-containing hydrogenation reaction catalyst with hydrogen gas in a stream of a solvent which does not react with copper oxide or metallic copper.

Precursors of copper-containing hydrogenation reaction catalysts include, but not limited to, those containing copper-chromium oxides, copper-zinc oxides, copper-iron oxides, copper-aluminum oxides and copper-silica oxides. It is preferable that the content of copper oxide is within the range of from 5 to 98% by weight, more preferably from 20 to 98% of the total weight of the catalyst precursor. These metal catalyst precursors may be carried on such carriers as silica, alumina, zirconium oxide, titanium oxide and silica-alumina. In such cases, the total weight of the catalyst precursor as mentioned herein includes the weight of the carrier.

The shape of the catalyst precursor to be formed may be optionally chosen, as long as it does not interfere with operation of the fixed bed reactor. Usually, cylindrically tableted or extruded catalyst precursors, or 1 to 20 mm spherically formed catalyst precursors are preferably used, since their production is easy and inexpensive.

Also, the inert solvent is a solvent which does not dissolve or irreversibly adsorb copper oxide or metallic copper and which does not form a compound with copper. Such solvents remain in a liquid state under the reducing conditions for activating the catalyst precursor, and preferably include glyceride oils, esters, alcohols, hydrocarbons, etc. Most preferable solvents include glyceride oils, fatty acid esters, aliphatic alcohols and hydrocarbons which do not adversely affect the quality of a desired alcohol produced according to the present invention, and these solvents may be used singly or in combination. Specifically, the glyceride oils are exemplified by monoglycerides, diglycerides and triglycerides comprising fatty acids having 6 to 22 carbon atoms. Such fatty acids include natural fatty acids of plant or animal origin derived from coconut oil, palm kernel oil, palm oil, beef tallow, lard and the like, and synthetic fatty acids. The fatty acid esters are exemplified by those formed between a fatty acid having at least one fatty acid group of 2 to 22 carbon atoms and an aliphatic alcohol having 1 to 22 carbon atoms. For example, esters formed between one of the above mentioned fatty acids and an aliphatic alcohol such as methanol, ethanol, propanol, butanol, hexanol, octanol, decanol, lauryl alcohol, myristyl alcohol, cetyl alcohol, stearyl alcohol and isostearyl alcohol. The aliphatic alcohols used as solvents are exemplified by those having 2 to 22 carbon atoms and at least one hydroxyl group which is in a liquid state under the reducing conditions for activating a catalyst precursor. Such aliphatic alcohols include octanol, decanol, lauryl alcohol, myristyl alcohol, cetyl alcohol, stearyl alcohol and isostearyl alcohol. The hydrocarbons are exemplified by liquid paraffin and cyclic hydrocarbons such as cyclohexane, cyclooctane, decalin, benzene, toluene, xylene and naphthalene.

However, other inert solvents may also be used, as long as the residual impurities contained in solvents do not significantly affect the quality of the alcohol produced. Such solvents include ethers, aldehydes and ketones which are in a liquid state under reducing conditions for activating the catalyst precursor. In addition, the alkyl group moiety of these organic compounds, including the above-mentioned esters and alcohols, comprises one or more kinds selected from the group consisting of straight chain, branched chain, alicyclic ring, and aromatic ring.

The velocity for supplying such a solvent is preferably 0.1 to 5.0/hr, more preferably 0.1 to 3.0/hr as a liquid hourly space velocity. When the supply rate is lower than 0.1/hr, the catalyst precursor is unevenly wetted with the solvent so that the catalyst precursor may partially undergo gas phase reduction. When the supply velocity exceeds 5.0/hr, the required amount of solvent becomes large and thus it is economically undesirable, though catalyst reduction is not hampered at all. The temperature is normally kept in the range of from 20° to 60° C. when the solvent is introduced into the reactor so that the reduction of a catalyst precursor can be initiated under conditions as mild as possible. The temperature is then increased up to the level for reductive activation mentioned below.

The method of the present invention for preparing a copper-containing hydrogenation reaction catalyst is carried out while supplying hydrogen gas, or a mixture of hydrogen and inert gas, as a reducing agent to contact with a catalyst precursor.

The inert gas for diluting hydrogen may include nitrogen, helium, argon, methane and the like. The hydrogen concentration in the gas mixture is optionally chosen within the range of from 0.1% to 100% by volume, but it is desirable from the viewpoint of saving the activation time that hydrogen is used in concentrations to make the partial hydrogen pressure one atm or higher.

Preferably, the gas is supplied under a normal pressure or an increased pressure up to 300 atm in a stream of a solvent. Gas supply pressures above 300 atm are economically disadvantageous because of increased equipment burden, though the effect of the invention can be obtained.

Also, the gas is preferably supplied at a gas hourly space velocity of from 50 to 10000/hr, more preferably from 100 to 5000/hr. When gas hourly space velocities are below 50/hr, it is difficult to adequately remove the heat and the water produced upon reduction, resulting in decreased catalyst performance. Gas hourly space velocities exceeding 10000/hr are disadvantageous in view of equipment requirements. The temperature of the gas introduced into the reactor is normally kept in the range of from 20° to 60° C. for the same reason as for the solvent introduction mentioned above. The temperature is then increased up to the level for reductive activation as mentioned below.

In the present invention, the temperature at which reductive activation is carried out is very important. This invention is characterized in that a catalyst precursor is reduced by liquid phase reduction within the temperature range of from 50° to 140° C., preferably from 70° to 140° C., while supplying a solvent and a gas as stated above. In the present specification, the temperature which mostly contributes to the liquid phase reduction is referred to as the reductive activation temperature. For example, an inert solvent or hydrogen gas is introduced at a temperature in the range of from 20° to 60° C. in order to initiate the reductive activation of a catalyst precursor under the conditions as mild as possible, and then the temperature is raised to a level of reductive activation. Though the reductive activation of a catalyst precursor may proceed to a limited extent during the initial period of temperature elevation, the temperature in this period is not referred to as the reductive activation temperature, because the reductive activation proceeds mainly in the temperature range of from 50° to 140° C. When the temperature is kept constant, for example, at 130° C. for a certain period with the purpose of reducing the precursor, it is described as "the liquid phase reduction is carried out at 130° C." When the reductive activation temperature is less than 50° C., the rate of reductive activation is likely to become inadequate and the object of the present invention cannot be sufficiently achieved. When the reductive activation temperature exceeds 140° C., it is not preferable from the economic viewpoint because the ester and alcohol are likely to deteriorate. Specifically, when the solvent is an ester, it is hydrolyzed with water produced upon catalyst reduction to yield fatty acids which are a catalyst poison to copper-containing catalyst, and therefore it is required to decrease the content of fatty acids before the ester is used again as the starting material for alcohol production. Also, when fatty acid is formed during reduction of the catalyst precursor, dissolution of copper oxide and metallic copper occurs to change the quality of catalyst surface. When an alcohol is used as the solvent, the reaction by which two alcohol molecules are converted to an ester wax is accelerated as the catalyst is activated, the ester wax causing a significant lowering of alcohol purity. In addition, with an increase in the reduction temperature, the amount of hydrocarbons generated by degradation of alcohol is increased, and therefore it is not economically advantageous.

The liquid phase reduction in the present invention may be carried out while keeping a constant temperature for most of the reduction time, or while raising the temperature within the range described above over the period of the reduction. It may also be carried out by combining the above two conditions. The temperature may be raised continuously or discontinuously, and the heating speed may not necessarily be constant. The effect of the present invention is not influenced by whether the temperature is kept constant for a certain period of time or it is kept changing.

The duration of the liquid phase reduction varies depending on the reduction temperature mentioned above, and it is normally more than 1.5 hours, preferably 6 to 100 hours, when the liquid phase reduction is carried out in the temperature range of from 50° to 140° C. When the duration is less than 1.5 hours, adequate catalytic activation cannot be achieved. When the reduction time exceeds 100 hours, it is not acceptable from the economic viewpoint, though sufficient catalytic performance can be obtained.

The rate at which the temperature is raised is normally 0.5° to 40° C./hr, preferably 1° to 30° C./hr, and most preferably 5° to 20° C./hr. Heating rates below 0.5° C./hr are disadvantageous in that too much time is required for the reductive activation of the catalyst precursor, though the effect of the present invention can be obtained. Heating rates exceeding 40° C./hr are also disadvantageous in that accumulation of reduction heat generated by rapid catalyst reduction causes a rapid rise in temperature and makes it difficult to control the reducing reaction.

As mentioned above, in a preferred embodiment of the method for preparing a copper-containing hydrogenation reaction catalyst of the present invention, a solvent and hydrogen gas, or a mixture of hydrogen gas and an inert gas, are introduced in the temperature range of from 20° to 60° C.; and then the temperature is raised to the reduction temperature range of from 50° to 140° C., and in this temperature range a liquid phase reduction of a catalyst precursor is carried out. According to this method, significant improvement in catalyst activity can be achieved without causing deterioration of the solvent.

The copper-containing hydrogenation reaction catalyst thus obtained by the method of the present invention can be used mainly for alcohol production in a fixed bed continuous reaction system, and it can also be used for various hydrogenation reactions, such as for an aldehyde group or a ketone group hydrogenation, olefin hydrogenation and a nitro group hydrogenation. Therefore, when liquid phase reduction of a precursor of a copper-containing hydrogenation reaction catalyst is carried out in a fixed bed reactor for continuous reaction, the resulting activated catalyst can be directly used for the subsequent production of alcohols or other products.

The method for producing an alcohol of the present invention is characterized in that a copper-containing hydrogenation reaction catalyst activated by the above-described method is used in the method for producing an alcohol by catalytic reduction of an organic carboxylic acid or an ester of organic carboxylic acid with hydrogen in a fixed bed continuous reaction system.

Organic carboxylic acids used as the starting material include natural fatty acids of animal or plant origin derived from coconut oil, palm kernel oil, palm oil, beef tallow, lard and the like, and synthetic fatty acids. The preferred ester of organic carboxylic acid is fats and oils or a fatty acid ester. The fats and oils are exemplified by monoglycerides, diglycerides and triglycerides comprising saturated or unsaturated fatty acids having 6 to 22 carbon atoms. The fatty acid ester is exemplified by straight or branched, or unsaturated fatty acid esters having one or more carbon atoms and one or more ester groups. Such fatty acid esters include formates, acetates, caproates, caprylates, caprates, undecenates, laurates, myristates, palmitates, stearates, isostearates, oleates, arachates, behenates, oxalates, maleates, adipates and sebacates. Here, the alcohol moiety of the fatty acid ester, not subject to limitation, comprises an aliphatic alcohol having 1 to 22 carbon atoms. Also, the ester to be hydrogenated in the present invention is not limited to fatty acid esters, and may be any one of alicyclic carboxylic acid esters such as cyclohexanecarboxylate, and aromatic carboxylic acid esters such as benzoate and phthalate, and derivatives thereof.

In the present invention, the fixed bed continuous reaction system is employed to hydrogenate the above-described organic carboxylic acids or esters of organic carboxylic acids. Although a solvent may be used for the hydrogenation reaction, it is desirable to carry out the reaction in the absence of a solvent in view of productivity. When a solvent is used, it is chosen from the group of solvents which do not adversely affect the reaction, such as alcohols, dioxane and paraffin. Reaction temperature is normally 130° to 300° C., preferably 160° to 250° C.; reaction pressure, 0.1 to 300 kg/cm$^2$. Also, the liquid hourly space velocity for the starting material supply is determined optionally according to reaction conditions, and is preferably within the range of from 0.2 to 5.0/hr in view of productivity or reactivity.

EXAMPLES

The present invention is hereinafter described in more details by means of the following working examples and comparative examples, but the present invention is not limited by them.

Example 1

First, a catalyst precursor, where CuO, ZnO and BaO are carried on TiO$_2$, is prepared by the method described in Example 5 of Japanese Patent Laid-Open No. 5-177140.

The obtained precursor powder is cylindrically tableted and then calcined at 400° C. for 2 hours to yield a formed catalyst precursor having a diameter of 3 mm, a height of 3 mm and the following weight composition: CuO:ZnO:BaO:TiO$_2$=33.0%:3.7%:3.3%:60.0%

Then 30 cc of the formed catalyst precursor thus obtained is packed in a fixed bed high-pressure flow reactor, hydrogen gas (100% concentration) is introduced at a flow velocity of 37 NL/hr (a gas hourly space velocity of 1230/hr) at a temperature of 40° to 50° C., and then lauryl alcohol (99.8% purity) is supplied at a flow velocity of 15 cc/hr (a liquid hourly space velocity of 0.5/hr). After the liquid and gas flow velocities are stabilized, the temperature is raised at a rate of 10° C./hr under a hydrogen pressure of 20 kg/cm$^2$ (gauge pressure) and maintained at 130° C. for 24 hours to carry out reductive activation of the catalyst precursor.

After completion of the reductive activation, the lauryl alcohol is replaced with a fatty acid methyl ester (a saponification value of 243) having a chain length distribution of from 8 to 18 carbon atoms, and a hydrogenation reaction is carried out at 230° C. while supplying hydrogen in an amount of 25 mole per mole of the fatty acid methyl ester under a pressure of 200 kg/cm$^2$ and at a liquid hourly space velocity of 1.0/hr.

The purity of lauryl alcohol at the completion of the reductive activation is determined by gas chromatography. The purity is 98.7%.

The catalytic activity is determined as a constant for the primary reaction rate per unit volume of the formed catalyst. Also, the reaction selectivity is expressed in terms of the amount of by-products such as hydrocarbons and ether compounds determined by gas chromatography.

The results are shown in Table 1.

TABLE 1

| Examples | Catalyst precursor Composition (% by weight) | Reductive activation conditions Pressure (kg/cm$^2$) | Temperature (°C.) | Solvent | Reduction time (hour) | Catalytic activity (Relative value)* | Selectivity (Relative value)* |
|---|---|---|---|---|---|---|---|
| Ex. 1 | CuO:ZnO:BaO:TiO$_2$ 33.0:3.7:3.3:60 | 20 | 130 | Lauryl alcohol | 24 | 1.14 | 0.55 |
| Ex. 2 | CuO:ZnO:BaO:TiO$_2$ 33.0:3.7:3.3:60 | " | 100 | Lauryl alcohol | 6 | 1.15 | 0.53 |
| Ex. 3 | CuO:ZnO:BaO:TiO$_2$ 33.0:3.7:3.3:60 | " | 80 | Lauryl alcohol | 24 | 1.02 | 0.58 |
| Ex. 4 | CuO:ZnO:BaO:TiO$_2$ 33.0:3.7:3.3:60 | " | Constant at 100° C. | Lauryl alcohol | 24 | 1.10 | 0.56 |
| Comp. Ex. 1 | CuO:ZnO:BaO:TiO$_2$ | 15 | 130 | Gas phase | 157 | 1 | 1 |

TABLE 1-continued

| Examples | Catalyst precursor Composition (% by weight) | Reductive activation conditions Pressure (kg/cm$^2$) | Temperature (°C.) | Solvent | Reduction time (hour) | Catalytic activity (Relative value)* | Selectivity (Relative value)* |
|---|---|---|---|---|---|---|---|
| Comp. Ex. 2 | CuO:ZnO:BaO:TiO$_2$ 33.0:3.7:3.3:60 | 20 | 200 | Lauryl alcohol | 6 | 1.24 | 0.54 |
| Ex. 5 | CuO:ZnO:BaO:TiO$_2$ 33.0:3.7:3.3:60 | 3 | 130 | Methyl ester | 6 | 1.05 | 0.55 |
| Ex. 6 | CuO:ZnO:BaO:TiO$_2$ 33.0:3.7:3.3:60 | 200 | " | " | 6 | 1.07 | 0.80 |
| Comp. Ex. 3 | CuO:ZnO:BaO:TiO$_2$ 33.0:3.7:3.3:60 | 3 | 200 | " | 6 | 1.29 | 0.83 |
| Ex. 7 | CuO:ZnO:BaO:TiO$_2$ 43.6:2.3:4.1:50.0 | 20 | 130 | Lauryl alcohol | 24 | 1.44 | 0.54 |
| Comp. Ex. 4 | CuO:ZnO:BaO:TiO$_2$ 43.6:2.3:4.1:50.0 | 15 | " | Gas phase | 160 | 1 | 1 |

*Exs. 1 to 6 and Comp. Exs. 2 and 3: Based upon the values obtained in Comp. Ex. 1.
*Ex. 7: Based upon the values obtained in Comp. Ex. 4.

Example 2

Reductive activation of the catalyst precursor as obtained in Example 1 is carried out in the same manner as in Example 1 except that it is conducted at 100° C. for 6 hours. By means of the activated catalyst thus obtained, hydrogenation of a fatty acid methyl ester is carried out according to the method described in Example 1. The purity of lauryl alcohol at the completion of reductive activation is 99.0%.

The results are shown in Table 1.

Example 3

Reductive activation of the catalyst precursor as obtained in Example 1 is carried out in the same manner as in Example 1 except that it is conducted at 80° C. for 24 hours. By means of the activated catalyst thus obtained, hydrogenation of a fatty acid methyl ester is carried out according to the method described in Example 1. The purity of lauryl alcohol at the completion of reductive activation is 99.7%.

The results are shown in Table 1.

Example 4

The formed catalyst precursor as obtained in Example 1 is packed in a reactor in the same manner as in Example 1. Lauryl alcohol of 99.8% purity is introduced at a flow velocity of 15 cc/hr (a liquid hourly space velocity of 0.5/hr) after nitrogen is introduced at a flow velocity of 37 NL/hr (a gas hourly space velocity of 1230/hr) at a temperature of from 40° to 50° C. After the flow velocities of the liquid and the gas above are stabilized, temperature starts to be raised at a velocity of 10° C./hr. When the temperature reaches 100° C., the nitrogen gas is replaced with hydrogen gas, and reductive activation of the catalyst precursor is carried out at 100° C. for 24 hours. According to the method described in Example 1, hydrogenation of a fatty acid methyl ester is carried out by means of the activated catalyst thus obtained. The purity of lauryl alcohol at the completion of the reductive activation is 98.7%.

The results are shown in Table 1.

Comparative Example 1

The formed catalyst precursor as obtained in Example 1 is packed in a reactor according to the method described in Example 1, and gas phase reductive activation of the precursor is carried out in the stream (a gas hourly space velocity of 250/hr) of 1.3 to 5.0 % by volume of hydrogen diluted with nitrogen gas under a pressure of 15 kg/cm$^2$ (gauge pressure) at 130° C. for 157 hours.

By means of the catalyst precursor thus obtained, hydrogenation of a fatty acid methyl ester is carried out under the conditions described in Example 1.

The results are shown in Table 1.

Comparative Example 2

Reductive activation of the catalyst precursor as obtained in Example 1 is carried out in the same manner as in Example 2 except that it is conducted at 200° C. for 6 hours. By means of the activated catalyst thus obtained, hydrogenation of a fatty acid methyl ester is carried out according to the method described in Example 2. The purity of lauryl alcohol at the completion of reductive activation is 90.0%. A significant reduction of alcohol purity is observed.

The results are shown in Table 1.

Example 5

According to the method of Example 1, the formed catalyst precursor as obtained in Example 1 is placed in the reactor. Then, hydrogen gas is introduced into the reactor at a flow velocity of 37 NL/hr (a gas hourly space velocity of 1230/hr), followed by introduction of a fatty acid methyl ester (a saponification value of 243, an acid value of 0.2) at a flow velocity of 15 cc/hr (a liquid hourly space velocity of 0.5/hr). After the flow velocities of the liquid and the gas above become stable, temperature is raised under a hydrogen pressure of 3 kg/cm$^2$. After the catalyst precursor is reductively activated at 130° C. for 6 hours, hydrogenation reaction is carried out under the reaction conditions described in Example 1. The acid value of the fatty acid methyl ester at the completion of the reductive activation is 0.6.

The results are shown in Table 1.

Example 6

According to the method of Example 5, reductive activation of the catalyst precursor as obtained in Example 1 is carried out in a solvent of a fatty acid methyl ester under a hydrogen pressure of 200 kg/cm$^2$ for 6 hours. Then, hydrogenation reaction is carried out under the same conditions as in Example 1. The acid value of the fatty acid methyl ester at the completion of reductive activation is 0.6.

The results are shown in Table 1.

Comparative Example 3

Reductive activation of the catalyst precursor is carried out by the same method as in Example 5 except that it is carried out at a temperature of 200° C. for 6 hours. Then, hydrogenation of a fatty acid methyl ester is carried out. Here, the acid value of the fatty acid methyl ester at the completion of the reductive activation is 5.0, indicating that fatty acids, catalyst poisons, are significantly increased. It is also found that degenerative change of the catalyst surface due to fatty acid formation leads to 1.5 time increase in the amount of by-products.

The results are shown in Table 1.

Example 7

A catalyst precursor comprising $TiO_2$ carrying CuO, ZnO and BaO on the surface thereof is prepared by the method disclosed in Example 5 of Laid-open Japanese Patent Publication No. 5-177140.

The powder of the catalyst precursor thus obtained is cylindrically tableted, and calcined at 400° C. for 2 hours to yield a formed catalyst precursor having a diameter of 3 mm, a height of 3 mm, and the following weight composition: $CuO:ZnO:BaO:TiO_2=43.6\%:2.3\%:4.1\%:50.0\%$.

Then, 30 cc of the formed catalyst thus obtained precursor is packed in a reactor in the same manner as described in Example 1, reductive activation is carried out. Then, by means of the activated catalyst thus obtained, hydrogenation of a fatty acid methyl ester is carried out according to the method of Example 1. The purity of lauryl alcohol at the completion of reductive activation is 99.1%.

The results are shown in Table 1.

Comparative Example 4

The formed catalyst precursor described in Example 7 is subject to gas phase reductive activation for 160 hours according to the method described in Comparative Example 1. By means of the activated catalyst thus obtained, hydrogenation of a fatty acid methyl ester is carried out according to the method described in Example 1.

The results are shown in Table 1.

Example 8

A commercially available copper-chromium catalyst precursor, which is a cylindrical tablet having a diameter of 3 mm and a height of 3mm and has the weight composition of $CuO:Cr_2O_3:MnO_2=45.0\%:45.0\%:5.0\%$, is subject to reductive activation according to the method described in Example 1. Then, by means of the activated catalyst thus obtained, hydrogenation of a fatty acid methyl ester is carried out under the conditions described in Example 1. The purity of lauryl alcohol at the completion of the reductive activation is 98.9%.

The results are shown in Table 2.

TABLE 2

| Examples | Catalyst precursor Composition (% by weight) | Reductive activation conditions Pressure (kg/cm²) | Temperature (°C.) | Solvent | Reduction time (hour) | Catalytic activity (Relative value)* | Selectivity (Relative value)* |
|---|---|---|---|---|---|---|---|
| Ex. 8 | $CuO:Cr_2O_3:MnO_2$ 45.0:45.0:5.0 | 20 | 130 | Lauryl alcohol | 24 | 1.25 | 0.58 |
| Comp. Ex. 5 | $CuO:Cr_2O_3:MnO_2$ 45.0:45.0:5.0 | 15 | 130 | Gas phase | 160 | 1 | 1 |
| Ex. 9 | $CuO:Fe_2O_3:Al_2O_3$ 32:32:36 | 20 | 130 | Lauryl alcohol | 24 | 1.22 | 0.62 |
| Comp. Ex. 6 | $CuO:Fe_2O_3:Al_2O_3$ 32:32:36 | 15 | 130 | Gas phase | 160 | 1 | 1 |

*Exs. 8 and 9: Based upon the values obtained in Comp. Exs. 5 and 6, respectively.

Comparative Example 5

The formed catalyst precursor described in Example 8 is subject to gas phase reduction with diluted hydrogen for 160 hours according to the method described in Comparative Example 1. By means of the catalyst thus activated, hydrogenation of a fatty acid methyl ester is carried out under the reaction conditions described in Example 1.

The results are shown in Table 2.

Example 9

The powder of a catalyst precursor prepared by the method disclosed in Example 1 of Japanese Patent Examined Publication No. 58-50775 is formed by extrusion with bentonite to yield a noodle shaped catalyst precursor having a length of 5 mm, a diameter of 2 mm and the following weight composition: $CuO:Fe_2O_3:Al_2O_3=32\%:32\%:36\%$.

Then, 30 cc of the formed catalyst precursor thus obtained is subject to reductive activation and hydrogenation of a fatty acid methyl ester is carried out according to the method described in Example 1. The purity of lauryl alcohol at the completion of the reductive activation is 99.1%.

The results are shown in Table 2.

Comparative Example 6

The formed catalyst precursor described in Example 9 is subject to gas phase reductive activation with diluted hydrogen for 160 hours according to the method described in Comparative Example 1. By means of the catalyst thus activated, hydrogenation of a fatty acid methyl ester is carried out under the conditions described in Example 1.

The results are shown in Table 2.

These results presented above demonstrate that all catalysts prepared by the method for preparing a copper-containing hydrogenation reaction catalyst of the present invention are excellent in catalytic activity and selectivity. On the other hand, the catalysts obtained by gas phase reduction (Comparative Examples 1, 4, 5 and 6) are proved to be inferior in catalytic activity and selectivity. Although the catalysts obtained by liquid phase reduction at a high temperature (Comparative Examples 2 and 3) exhibit good catalytic activities and selectivities, there are observed significant reductions in the purities of alcohol and fatty acid methyl ester and degenerative changes of the catalyst surfaces due to fatty acids formed during the reductive activation.

The present invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for producing an alcohol, comprising the steps of:

reducing a precursor of a copper-containing hydrogenation catalyst with hydrogen gas or a mixture of hydrogen and an inert gas by liquid phase reduction in a stream of a solvent which does not react with copper oxide or metallic copper, in a fixed bed continuous reaction system in temperature range of from 50° to 140° C.; and reducing an organic carboxylic acid or an ester thereof by catalytic reduction with hydrogen.

2. The method according to claim 1, wherein the liquid phase reduction is carried out for more than 1.5 hours.

3. The method according to claim 1, wherein the hydrogen gas or the mixture of hydrogen and the inert gas is supplied at a gas hourly space velocity of from 50 to 10000/hr.

4. The method according to claim 1, wherein the solvent is supplied at a liquid hourly space velocity of 0.1 to 5.0/hr.

5. The method according to claim 1, wherein the organic carboxylic acid ester is fats and oils or fatty acids esters.

6. The method according to claim 1, wherein the solvent is selected from the group consisting of glyceride oils, fatty acid esters, aliphatic alcohols, hydrocarbons, and mixtures thereof.

7. The method according to claim 1, wherein the precursor of the copper-containing hydrogenation catalyst is selected from the group consisting of copper-chromium oxides, copper-zinc oxides, copper-iron oxides, copper-aluminum oxides, copper-silica oxides, and mixtures thereof.

8. The method according to claim wherein the content of copper oxide is in the range of from 5 to 98% by weight of the total weight of the catalyst precursor.

9. The method according to claim 1, wherein the solvent and the hydrogen gas or the mixture of hydrogen and the inert gas are introduced in a temperature range of from 20° to 60° C., and then the temperature is continuously or discontinuously raised to the temperature range from 50° to 140° C.

10. The method according to claim 9, wherein the rate at which the temperature is raised is 0.5° to 40° C./hr.

11. The method according to claim 1, wherein the catalytic reduction with hydrogen is conducted at a temperature from 130° to 300° C. and at a pressure from 0.1 to 300 kg/cm².

12. The method according to claim 1, wherein said organic carboxylic acid is selected from the group consisting of natural fatty acids of animal or plant origin derived from coconut oil, palm kernel oil, palm oil, beef tallow, lard and synthetic fatty acids.

13. The method according to claim 5, wherein said fats and oils are selected from the group consisting of monoglycerides, diglycerides and triglycerides, each fatty acid moiety being saturated or unsaturated fatty acids having 6 to 22 carbon atoms.

14. The method according to claim 5, wherein said fatty acid ester is selected from the group consisting of formates, acetates, caproates, caprylates, caprates, undecenates, laurates, myristates, palmitates, stearates, isostearates, oleates, arachates, behenates, oxalates, maleates, adipates and sebacates, wherein the alcohol moiety of said fatty acid ester comprises an aliphatic alcohol having 1 to 22 carbon atoms.

15. The method according to claim 1, wherein the organic carboxylic acid ester is an alicylic carboxylic acid ester or an aromatic carboxylic acid ester.

16. A method for producing an alcohol, comprising the steps of:

providing a precursor of a copper-containing hydrogenation catalyst in a fixed bed continuous reaction system;

introducing a stream of a solvent which does not react with copper oxide or metallic copper and a reducing gas of hydrogen, or a mixture of hydrogen and an inert gas, in a temperature range from 20° to 60° C.;

reducing by liquid phase reduction said precursor of a copper-containing hydrogenation catalyst by continuously or discontinuously raising the temperature of the system in a range from 50° to 140° C.; and reducing an organic carboxylic acid or ester thereof by catalytic reduction with hydrogen.

* * * * *